United States Patent [19]

Kamentsky

[11] Patent Number: 4,487,839
[45] Date of Patent: Dec. 11, 1984

[54] IMMUNOASSAY METHODS EMPLOYING PATTERNS FOR THE DETECTION OF SOLUBLE AND CELL SURFACE ANTIGENS

[75] Inventor: Louis A. Kamentsky, Weston, Mass.

[73] Assignee: Ortho Diagnostic Systems Inc., Raritan, N.J.

[21] Appl. No.: 455,765

[22] Filed: Jan. 5, 1983

[51] Int. Cl.³ .................. G01N 33/52; G01N 33/58
[52] U.S. Cl. .................. 436/518; 436/524; 436/528; 436/537; 436/541; 436/542; 436/800; 436/804; 436/807; 436/808; 436/809; 436/823
[58] Field of Search ............ 436/528, 541, 542, 800, 436/804, 809, 823, 518, 524, 537, 807, 808

[56] References Cited

U.S. PATENT DOCUMENTS 3,941,876 3/1976 Marinkovich .................. 436/800
4,011,308 3/1977 Giaever .................. 436/525
4,031,197 6/1977 Marinkovich .................. 436/542

OTHER PUBLICATIONS

Walden, Diss. Abstracts B, vol. 41 (1980), pp. 561–562.
Deeloer et al., Chem. Abstracts, vol. 90 (1979) #68828q.

Primary Examiner—Christine M. Nucker
Attorney, Agent, or Firm—Mark A. Hofer

[57] ABSTRACT

Methods for determining the presence of antigens or antibodies in an aqueous sample or presence of antigens on the surface of cells. A preferred embodiment employs fluorescent antigens which compete with the sample antigens for antibody binding sites. The antibodies are deposited on a support surface means in alternating patterns. The surface means and fluorescence detector are translocated with respect to each other and a signal generated by the detection of the repeating pattern of fluorescence. The signal is analyzed by means of a gated integrator responsive to a gate track control means also located on the surface means. Immunoassay methods having increased sensitivity are thereby obtained.

64 Claims, 4 Drawing Figures

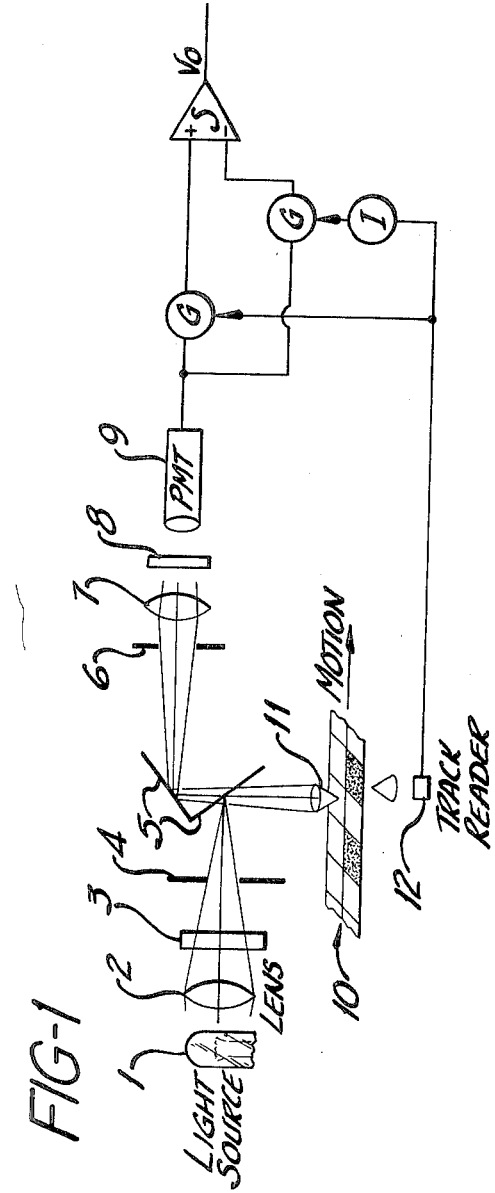

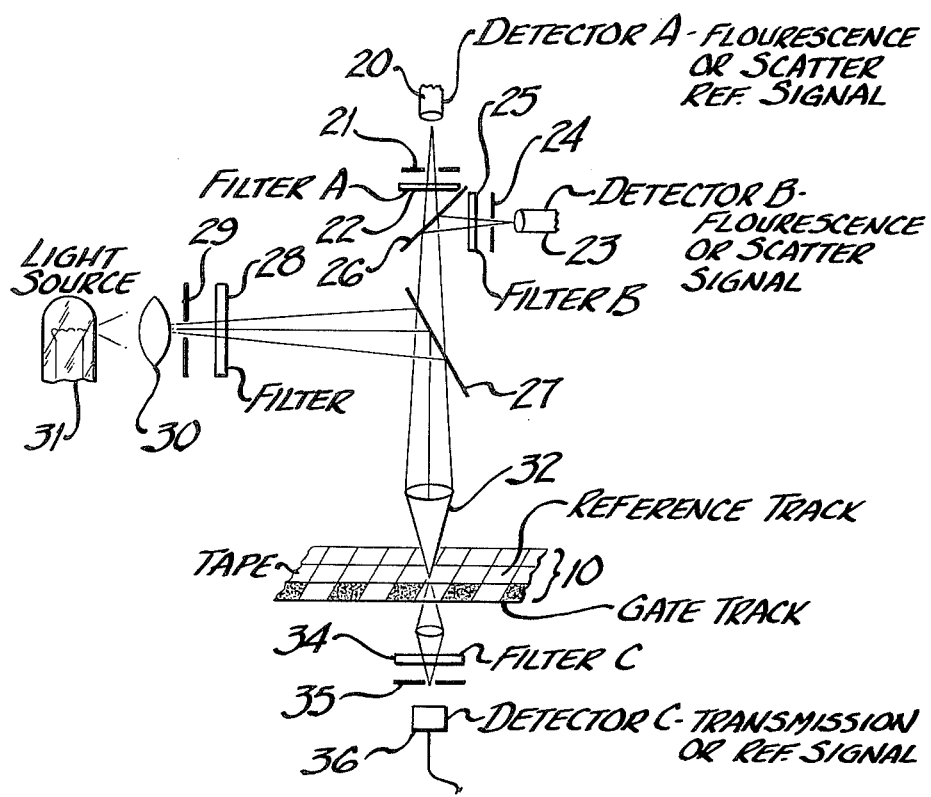

IMMUNOASSAY METHODS EMPLOYING PATTERNS FOR THE DETECTION OF SOLUBLE AND CELL SURFACE ANTIGENS

FIELD OF THE INVENTION

This invention relates generally to immunoassay methods useful for detecting soluble and cell surface antigens and more specifically, relates to methods employing patterns of immunological reactions formed on solid phase surfaces.

BACKGROUND OF THE INVENTION

The detection of specified antigens and/or their specific binding partners, antibodies, has in recent years become of utmost importance in both the research and clinical environment. The detection of antigens and antibodies can often be related to various disease states and consequently is of extreme usefulness in diagnosis as well as gaining basic understandings concerning the genesis of disease including cancer as well as the effectiveness of therapies therefor.

Consequently, improved methods for detecting antigens found in aqueous samples, i.e. soluble antigens, as well as antigens found on the surface of tissues and cells are constantly sought. Typically, immunoassay methods may be characterized by their speed/facility of employment and by their sensitivity.

It is therefore an object of the present invention to provide new and novel methods which are susceptible to use in automated and semi-automated instruments. It is another object to provide new immunoassay methods having a desirably high level of sensitivity to the antigens to be detected. It is a still further object to provide methods which incorporate a noise reduction technique for the generation of signals having superior signal-to-noise ratios.

SUMMARY OF THE INVENTION

In accordance with the objects of the present invention, methods are provided which permit the detection of antigens solubilized within a sample solution or located on the surface of cells by employing surfaces having appropriate antibodies (i.e., antibodies specific for the particular antigen to be detected) bound thereto in particularized patterns. These patterns, expediently produced by alternating areas with the presence and absence of antibodies, permit the generation of signals responsive to the presence of label having superior signal-to-noise ratios than those generally provided by conventional techniques.

Immunological reactions between antigens and antibodies will occur substantially only in or on those surface areas having antibodies attached thereto or deposited thereon but not in those areas having an absence of antibodies. Accessory labeled antigens are made to compete with antigens from the sample for antibody binding sites. By effecting translocation of the surface vis-a-vis a detector capable of detecting the label, a signal representing the difference in measurable levels of label between areas having antibodies and areas having no antibodies may be obtained. This repetitive signal can be expediently analyzed electronically and/or mathematically pursuant to well-known conventional methods to determine the quantity of antigens originally present in the sample.

Alternately, the so-called sandwich techniques may be employed whereby antigens or haptens, immunologically similar to the antigens to be detected are deposited on the surface, antibodies reacted therewith followed by addition of the sample containing the antigens to be detected. Finally, these exposed antigens are detected by the application of labeled antibodies. Detection of the label and subsequent signal handling would otherwise be identical to the competitive type procedures described.

BRIEF DESCRIPTION OF THE DRAWINGS

Further understanding of the principles and scope of the present invention may be had by reference to the drawings wherein:

FIG. 1 diagrammatically depicts the operation of the present invention in a preferred embodiment;

FIG. 1a illustrates the periodic, photomultiplier tube detected signal;

FIG. 2 shows the alternating pattern of deposition on a tape type surface; and

FIG. 3 illustrates an alternative embodiment of the present invention.

DETAILED DESCRIPTION AND BEST MODE

The principles of flow cytometry in combination with various labeling techniques such as those employing fluorescence can be applied to the determination and quantification of antigens present in a solution or on the surface of a cell. The use of fluorochromes or fluorescent dyes as a label lends itself particularly well to the present invention, however, other types of labels may be equally expedient. For the sake of simplicity, the discussion will be limited to the use of fluorescent dyes, however, it is understood, that one skilled in the art may employ other labels such as metal particles (colloidal gold), enzymes, radioisotopes or the like with equal facility.

A typical problem encountered with coventional immunoassay techniques is that of obtaining a sufficiently high signal-to-noise ratio in order to acquire the sensitivity desired. Typically, background fluorescence operates to mask the desired signal particularly when the signal is generated by a weak immunological reaction commonly occasioned by low antigen concentration. The present invention provides novel ways of circumventing this problem by utilizing the noise reduction technique of producing a periodic signal which is analyzed with the aid of a periodic reference signal. This is accomplished by reducing the antigen-antibody immunological reactions to specified and circumscribed areas on a surface such as that provided by a tape strip. Further, the invention is equally applicable to both competitive-inhibition type assays and sandwich type assays. In the former assay type, antibody to the desired antigen is deposited either on the surface or within the tape itself but in either case, in alternating specified locations so that a particular repeating pattern is produced while in the latter, antigen is deposited instead of antibody and an antibody-antigen-antibody bridge produced. Since the first type of assay is conceptually easier to understand, it will be fully described first.

A surface such as that provided by tape 10 is depicted in FIG. 2. Areas 11 have the antibody attached thereto while areas 12 are characterized by the absence of antibody. Areas 11 and 12 are limited to section 15 of tape 10 in contrast to a gate-track control section 16 described later. As may be readily appreciated, the shape of the areas may be varied greatly without departure from the objectives and principles of the present invention.

The tape, with antibodies attached, is then advantageously incubated with a known quantity of fluorescinated antigens which are as equally reactive (or at least at a comparatively known level) to the antibody deposited on the tape as are the antigens to be determined within the sample. Thus, the fluorescinated antigens and the sample antigens compete for available antibody binding sites. Unbound antigens are then ideally removed, advantageously accomplished by any standard washing technique such as by passing the tape through a bath or a spray.

With reference to FIG. 1, the tape is thereafter passed through an instrument capable of illuminating the tape by use of such standard optical devices as a light source 1; lenses 2, 11; filter 3; aperture 4; and mirrors 5; and measuring resultant bulk fluorescence again accomplished with such well-known arrangements as lens 11; mirrors 5; aperture 6; lens 7; filter 8 and photomultiplier tube 9. As the tape passes the focused light source, the alternating areas containing antibody and areas containing no antibody will be illuminated.

Those areas containing antibody can be expected to have some proportion of labeled antigen bound thereto. That amount will be dependent upon the level of competition for antibody binding sites generated by the antigens in the sample. Thus, in areas having no antibodies, and consequently no fluorescent antigens bound thereto, a very low or nonexistent signal of fluorescence will be measured. If manufactured perfectly, these areas would provide virtually no signal but in practicality, the representative signal will have some elevated, albeit noisy level ($V_1$ in FIG. 1A idealized in the figure as a perfectly constant level) representative of the background. In contrast, in those areas having antibody and consequently some amount of fluorescinated antigen bound thereto, a higher level signal $V_2$ will be detected by the photomultiplier tube (PMT). Analysis of the signal will be keyed by the gate control track and associated circuit depicted in FIG. 1 and discussed hereafter. Due to the relative translocation of the size limited area vis-a-vis the detector (i.e., it may be advantageous to move the detector rather than the tape), this PMT derived signal will be periodic in nature and by capitalizing on this characteristic, a superior signal-to-noise signal may be obtained. The difference between the high level and low level of fluorescence will be inversely related to the amount of antigen present in the sample or serum and may be enhanced by a switched or gated summing technique as described below.

FIG. 1a graphically shows the type of signal resultant from the PMT of the present invention. It is to be understood that the relative magnitudes of $V_1$ and $V_2$ are not drawn to scale but rather, have been drawn to emphasize the periodic nature of the waveform, their difference from ground (OV) and further illustrate ideal square-wave signals. In reality the detected signal will reflect physical and electronic imperfections of the system such as noise, imperfect area boundaries on the surface and the like.

Nonetheless the difference in levels, i.e., $V_2 - V_1$, where $V_2$ equals the level of fluorescence measured in areas of the tape containing antibody and $V_1$ is the level of fluorescence measured in areas containing no antibody, may be advantageously enhanced using a gated integrator.

A gated integrator is a summing device that operates as follows: signals are integrated positively or negatively at time intervals that are synchronized with a gate track (described below). The difference $V_2 - V_1$ in each signal is summed (integrated) with respect to the previous difference signals. Thus, the desired signal component $V_2$ will add coherently to the previous desired signal components, prior $V_2$s, because these desired components are integrated positively while background signals $V_1$s are integrated negatively. This switching of positive or negative integration is accomplished by gating the PMT signal to the positive or negative ports of a standard integrator in response to a signal derived from the gate track reader. The gate track reader signal is fed to a gate and an inverter to a gate as depicted in FIG. 1. The gates control the input of the PMT signal to the integrator. Thus, judicious timing of the physical and electronic aspects of this invention will permit summing the difference in PMT signals in order to add desired signal components minus the background signals.

With additional reference to the figures, the gate control track 16 may be advantageously located proximal to the regions containing antibody and indicates the beginning and end of the regions containing antibody. Additionally, such a gate control track may be advantageously employed to permit coating different areas of the tape, disk or other surface with various types of antibodies or multiple controls. Thus, the control track could code for the presence of various test materials, antibodies, and/or controls as well as different tests.

The advantage to many areas particularly in the advantageous stripe-type format as opposed to a limited number of areas, i.e., one sample and one reference location, is that nonspecific binding or other spatial inhomogeneities for binding antigen to the substrate may have relatively large spatial periods that are equal to or greater than the dimensions of the sample and reference areas. By using many stripes at a higher spatial frequency than these background inhomogeneities, the resulting, slowly varying background detection signal can be rejected for the most part by the use of the aforedescribed periodic gating or gated integrator.

In the case of the alternative sandwich type assay, antigens having immunologically similar reactivity to the antigens to be detected, i.e., they may be haptens as that term is commonly understood in the art, are deposited on the surface instead of antibodies. Parenthetically, it is appropriate to note that in this format, the invention may be used to detect the presence of antibodies in a fluid sample and thus will find yet further advantageous and important utility in the diagnostic arena.

Then, through a series of immunlogical reactions, a sandwich of alternating antibody-antigen levels is created. The surface antigens are reacted with an excess of antibody so that all antigenically reactive sites are covered. The sample with antigens is reacted therewith followed by reaction with labeled antibody. The labeled antibody will thus only attach to those antigenic sites supplied by the sample antigens and consequently, the level of detectable label can be related to the quantity and presence of antigen in the sample. The detection and analysis of the PMT signal (i.e., the detectable label) is in all other respects identical to that described above.

Still another and simpler sandwich technique involves the deposition of a first antibody on the surface specific for the sample antigens to be detected. After contacting the sample with the attached first antibody and removing unreacted materials, a second labeled antibody is allowed to react with the antigen but at a different epitopic site than that for which the first antibody is specific. The subsequent detection and analysis are as previously described.

Similarly, the principles of the present invention may be used to determine the presence of selected cell surface antigens or presence of cells containing such surface antigens. This may be accomplished by contacting the cells with a surface having attached thereto in specified areas the antibody specific for the cell surface antigen to be detected. By virtue of the standard immunological reaction, the cells having the desired cell surface antigens are attached to those areas of the tape containing the antibody.

Alternatively, antigens may be advantageously employed to coat specific areas of the tape (antigens are often more stable and thus easily manipulated than antibodies) and the sandwich technique or antibody bridge used to attach the cells containing the antigens of interest with the antigens present on the tape. In either case, the cells are then advantageously stained employing techniques conventional in the art. For instance, the cells may be stained with fluorescein diacetate which, in free solution is not fluorescent since the fluorescein (fluorescent portion) is quenched by the presence of the acetate moiety. Such a stain is typically adsorbed into the cell where it, in the presence of cellular esterase which cleaves off the acetate moiety, becomes fluorescent.

In yet another embodiment, the present invention may be employed to determine the presence of serum antibodies specific for cellular antigens such as the red blood cell typing antigens (A, B, AB, O, D). Such a test would be accomplished in the following manner. Cells containing the blood type-specific antigens are applied to specified areas of the tape or other surface which areas are coded by the gate control track. The tape treated in this manner is then passed through the sample serum under conditions appropriately adjusted to allow an immunological reaction between the cells present on the tape and the antibodies present in the serum. The tape is then washed of unreacted materials such as by spraying or by subsequent baths, and passed through a fluorescinated Coombs serum. Subsequently, the tape is read by a device such as that described above and fluorescence detected whereupon, with the aid of the gate control track, the blood type of an individual or animal may be determined.

Various alternatives to the tape may be advantageously employed and include, for example, such surfaces as a disk having radii defined sectors which alternately contain and do not contain antibody. Clearly, in such an embodiment, the preferred motion (or effective translocation with respect to the detector) would be rotary as opposed to the linear type of motion associated with the tape. Still yet another alternative would include the preparation of a surface such as the photoslide which may be completely illuminated and the detector moved to accomplish piecemeal interrogation or detection of specified areas. It is to be understood that with appropriate alterations, all of these alternative embodiments may be substituted for the tape in the prior discussion.

Additionally, alternatives to the use of cells may be advantageously employed in various of the above embodiments and would include, for instance, the use of latex particles. Such particles may be preferable as they are typically more capable of withstanding harsh mechanical and/or chemical treatment than are cells. Also, latex particles may prove more useful for optimizing coating uniformity and edge definition.

Other principles of light based flow cytometry apparatus, such as those obtainable from the assignee hereof, may be employed in conjunction with the methods and principles of the present invention. For instance and with reference to FIG. 3, alternatives to the detection of bulk fluorescence include the detection of light reflected from the tape (detectors 20 and 23), light transmitted or absorbed by the tape (detector 36), intrinsic fluorescence versus bound fluorescence and the detection of multiple fluorescent colors (detectors 20, 23). For example, one color may be employed specifically for the antibody and a second color tagged to a nonspecific antigen. Other embodiments contemplate the use of a tape 10 having a reference channel in addition to the gate control track and antibody areas. Such a reference signal may be particularly expedient for expanding the number or variety of tests which can be performed simultanteously on the surface. The placement of dichroic filters 28, 22, 25 and 34 as well as the detectors 20, 23, 34 themselves (along with apertures 21, 24, 35) for the particular detection of transmitted signal, scattered signal and fluorescence may be adjusted pursuant to techniques well-known in the art.

Further, it is to be understood that all antigen-antibody reactions discussed throughout the foregoing discussion depend upon appropriate conditions conducive for immunological reactions. It is also assumed that the selection of antigens, haptens or ligands and the selection of the ligand binding partner, i.e., antibody or reactive portions thereof, as all those terms are commonly employed, is in accordance with their reactivity, specificity and affinity so that immunological reactions will in fact ocur. Thus, the terms antigens and antibodies shall be understood to apply generically to this invention thus encompassing all possible immunological variations as conventionally understood in the immunoassay art.

Generally then, from the discussion, drawings as well as the disclosure, it may be readily apparent that one skilled in the art can derive various modifications of the present invention without departing from the spirit and scope thereof.

I claim:

1. A method for determining the presence of antigens in an aqueous sample comprising the steps of:
   (a) providing surface means having first antibodies, specific for the antigens to be determined, associated therewith in a specified pattern of areas, each area alternating with the presence and absence of said first antibodies;
   (b) further providing an aqueous solution containing a known quantity of labeled antigens having substantially the same reactivity with said first antibodies as the antigens to be determined;
   (c) contacting the aqueous sample and the aqueous solution with said surface means under conditions appropriate for permitting an immunological reaction to occur whereby said labeled and sample antigens compete for binding sites on said first antibodies;
   (d) illuminating at least one first area having first antibodies associated therewith and detecting the effect of said illumination on said label associated with said area by detection means for providing a first signal responsive to the presence of said labeled antigens;

(e) translocating said surface means with respect to said detector means and further illuminating at least one second area having an absence of first antibodies associated therewith and detecting the effect of said illumination on said label associated with said area whereby a second signal responsive to the presence of said labeled antigens is provided; and (f) analyzing said first and second signals whereby the presence of antigens in said aqueous sample may be determined based on the relative absence or presence of bound labeled antigen in said first area in comparison to said second area.

2. The method as provided in claim 1 wherein said providing step comprises providing surface means further comprising gate track control means, corresponding to the patterned areas of antibody presence and absence on said surface means, and said analyzing step further comprises detecting said gate track control means for enabling the analyzing step by associating said first and second signals with said first and second areas respectively.

3. The method as provided in claim 2 wherein the analyzing step comprises processing said first and second signals with gated integrator means whereby detecting said gate track control means enables said gated integrator means to positively integrate said first signals and negatively integrate said second signals from said detection means whereby the presence of said antigen in said aqueous sample may be determined.

4. The method as provided in claim 3 wherein said illuminating step comprises illuminating a fluorescent dye label at a light frequency which causes the label to fluoresce, and the step of detecting the effect of said illumination comprises detecting bulk fluorescence associated with said label.

5. The method as provided in claim 4 further comprising the step of removing said antigens to be determined and said labeled antigens which have not reacted immunologically with said first antibodies on said surface means by washing said surface means.

6. The method as provided in claim 3 wherein the step of detecting the effect of said illumination comprises detecting bulk fluorescence.

7. The method as provided in claim 1 wherein said providing step comprises providing a generally rectangular tape adapted for substantially linear motion.

8. A method for determining within a sample the presence of cells having a specified surface antigen, comprising the steps of:

(a) providing surface means having a pattern of areas alternating with the presence and absence of first antibodies associated therewith and specific for the surface antigens to be determined;

(b) contacting said sample containing the cells with said surface means under conditions appropriate to allow an immunological reaction to occur;

(c) staining the cells which have immunologically reacted with a detectable label;

(d) illuminating said surface means and detecting the effect of said illumination whereby a first signal responsive to the presence of said label in an area having antibodies associated therewith is generated;

(e) further illuminating said surface means and further detecting the effect of said illumination whereby a second signal responsive to the presence of said label in an area having an absence of antibodies associated therewith is generated; and (f) analyzing said first and second signals and determining the presence of cells having a specific surface antigen based on the association of said label with said area having antibodies specific for said cellular surface antigen.

9. The method as provided in claim 8 wherein the step of staining the cells is accomplished by applying to the cells an effective solution of fluorescein diacetate.

10. The method as provided in claim 8 further comprising the step of removing unbound cells prior to the detecting steps.

11. The method as provided in claim 8 wherein said analyzing step is enabled by additionally detecting gate track control means associated with said surface means and corresponding to the pattern of antibody presence and absence on said surface means whereby said first and second signals are identified with areas of presence and absence of said first antibodies respectively.

12. The method as provided in claim 10 wherein said analyzing step is enabled by additionally detecting gate track control means associated with said surface means and corresponding to the pattern of antibody presence and absence on said surface means whereby said first and second signals are identified with areas of presence and absence of said first antibodies respectively.

13. The method as provided in claim 11 wherein based on detecting said gate track control means said analyzing step comprises processing said first and second signals with gated integrator means whereby the presence of cells containing the specified surface antigen may be determined.

14. The method as provided in claim 12 wherein based on detecting said gate track control means said analyzing step comprises processing said first and second signals with gated integrator means whereby the presence of cells containing the specified surface antigen may be determined.

15. The method as provided in claim 8 further comprising detecting gate track control means associated with said surface means and corresponding to the pattern of antibody presence and absence on said surface means for controlling gated integrator means whereby said first detected signals are integrated positively and said second detected signals are integrated negatively and the presence of cells containing the specified surface antigen may be determined.

16. A method for determining the presence of cells having a specified surface antigen, said cells present within a sample, comprising the steps of:

(a) providing surface means having second antigens applied thereto in a specified pattern of areas alternating with the presence and absence of said second antigens;

(b) providing an antibody-complex specific for the specified cell surface antigen and for the second antigen whereby, after allowing an immunological reaction between said antibody-complex, said cell, and said second antigen, an antibody bridge between the surface means and the cells may be formed;

(c) permitting, under appropriate conditions, said immunological reaction to occur;

(d) staining the cells with a detectable label;

(e) illuminating an area of said surface means having second antigens present and detecting the effect of said illumination on said labeled cells whereby a first signal responsive to the presence of label is generated;

(f) illuminating an area of said surface means having second antigens absent and detecting the effect of said illumination on said labeled cells whereby a second signal responsive to the presence of label is generated; and (g) analyzing said first and second signals whereby the presence of cells having a specified surface antigen may be determined.

17. The method as provided in claim 16 wherein the step of staining the cells is accomplished by applying to the cells a solution of fluorescein diacetate.

18. The method as provided in claim 16 further comprising the step of removing unbound cells prior to the label detecting steps.

19. The method as provided in claim 16 wherein said providing step comprises providing surface means having gate track control means corresponding to the patterned areas of antigen presence and absence on said surface means, and said analyzing step further comprises detecting said gate track control means for enabling the analyzing step by identifying said first and second signals with said areas having a presence and absence of second antigens respectively.

20. The method as provided in claim 18 wherein said providing step comprises providing surface means having gate track control means corresponding to the patterned areas of antigen presence and absence on said surface means, and said analyzing step further comprises detecting said gate track control means for enabling the analyzing step by identifying said first and second signals with said areas having a presence and absence of second antigens respectively.

21. The method as provided in claim 19 wherein said analyzing step comprises processing said first and second signals with gated integrator means in response to said gate track control means whereby said first signals are integrated positively and said second signals are integrated negatively and the presence of cells containing the specified surface antigen may be determined.

22. The method as provided in claim 20 wherein said analyzing step comprises processing said first and second signals with gated integrator means in response to said gate track control means whereby said first signals are integrated positively and said second signals are integrated negatively and the presence of cells containing the specified surface antigen may be determined.

23. A method for determining the presence of antigens in an aqueous sample comprising the steps of:

(a) providing first antibodies and surface means having second antigens with substantially the same immunological reactivity with said first antibodies as the antigens to be determined, said second antigens associated with said surface in a specified pattern of areas, each area of presence alternating with an area of absence of said second antigens;

(b) immunologically reacting substantially all said second antigens with said first antibodies and removing substantially all unbound first antibodies;

(c) contacting the aqueous sample with said surface means under conditions appropriate for permitting an immunological reaction to occur whereby said antigens to be determined may be bound to said first antibodies;

(d) further providing an aqueous solution containing second labeled antibodies immunologically reactive with said antigens to be determined under conditions appropriate for permitting an immunological reaction to occur whereby said second labeled antibodies may be bound to said antigens to be determined if present;

(e) illuminating an area of said surface means having second antigens present and detecting the presence of said label whereby a first signal is generated;

(f) illuminating an area of said surface means having an absence of second antigens and detecting the presence of said label whereby a second signal is generated; and (g) analyzing said first and second signals whereby the presence of antigens in said aqueous sample may be determined.

24. The method as provided in claim 23 further comprising the step of detecting gate track control means associated with said surface means and corresponding to the pattern of second antigen presence and absence on said surface means and for enabling the analyzing step.

25. The method as provided in claim 24 wherein the analyzing step comprises processing said first and second signals with gated integrator means based on said gate track control means whereby said first signals are integrated positively and said second signals are integrated negatively whereby the presence of said antigen in said aqueous sample may be determined.

26. The method as provided in claim 25 wherein the further providing step comprises providing second antibodies labeled with a fluorescent dye, said illuminating steps comprise illuminating at a frequency of light which causes the label to fluoresce, and the step of detecting the effect of said illumination comprises detecting bulk fluorescence associated with said label.

27. The method as provided in claim 26 further comprising the step of removing, prior to said illuminating step, substantially all unbound second labeled antibodies which have not reacted immunologically by washing said surface means.

28. The method as provided in claim 26 wherein the step of detecting the effect of said illumination comprises detecting bulk fluorescence.

29. The method as provided in claim 23 wherein said providing step comprises providing surface means comprising a generally rectangular tape adapted for substantially linear motion.

30. A method for determining the presence of antigens in an aqueous sample comprising the steps of:

(a) providing surface means having first antibodies specific for a first epitopic site on said antigens to be determined, and which are associated with said surface in a specified pattern of areas, each area alternating with the presence and absence of said first antibodies;

(b) contacting the aqueous sample with said surface means under conditions appropriate for permitting an immunological reaction to occur whereby said antigens to be determined may be bound to said first antibodies;

(c) further providing an aqueous solution containing second labeled antibodies immunologically reactive with a second epitopic site on said antigens to be determined under conditions appropriate for permitting an immunological reaction to occur whereby said second labeled antibodies may be bound to said antigens to be determined if present;

(d) illuminating an area having said first antibodies present and detecting the effect of said illumination on said label whereby a first signal responsive to the presence of said labeled antibodies is provided;

(e) illuminating an area having an absence of said first antibodies and detecting the effect of said illumination on said label whereby a second signal responsive to the presence of said labeled antibodies is provided; and (f) analyzing said first and second signals whereby the presence of antigens in said aqueous sample may be determined.

31. The method as provided in claim 30 further comprising detecting gate track control means associated with said surface means and corresponding to the pattern of said first antibody presence and absence on said surface means for enabling the analyzing step.

32. The method as provided in claim 30 wherein the analyzing step comprises processing said first and second signals with gated integrator means said integrator being gated in response to the detection of said gate track control means whereby the presence of said antigen in said aqueous sample may be determined.

33. The method as provided in claim 32 wherein the further providing step comprises providing second antibodies labeled with a fluorescent dye, said illuminating steps comprise illuminating at a frequency of light which causes the label to fluoresce, and the step of detecting the effect of said illumination comprises detecting bulk fluorescence associated with said label.

34. The method as provided in claim 33 further comprising the step of removing, prior to said illuminating steps, substantially all unbound second labeled antibodies which have not reacted immunologically by washing said surface means.

35. The method as provided in claim 33 wherein the step of detecting the effect of said illumination comprises detecting bulk fluorescence.

36. The method as provided in claim 30 wherein said providing step comprises providing surface means comprising a generally rectangular tape adapted for substantially linear motion.

37. The method as provided in claim 4 further comprising the step of removing said antigens to be determined and said labeled antigens which have not reacted immunologically with said first antibodies on said surface means by spraying said surface means.

38. The method as provided in claim 4 further comprising the step of removing said antigens to be determined and said labeled antigens which have not reacted immunologically with said first antibodies on said surface means by washing and spraying said surface means.

39. The method as provided in claim 3 wherein the step of detecting the effect of said illumination comprises detecting light reflected from said surface means.

40. The method as provided in claim 3 wherein the step of detecting the effect of said illumination comprises detecting light transmitted through said surface means.

41. The method as provided in claim 3 wherein the step of detecting the effect of said illumination comprises detecting bulk fluorescence and intrinsic fluorescence of said surface means for use as a reference whereby the true level of bulk fluorescence may be assessed.

42. The method as provided in claim 3 wherein the step of detecting the effect of said illumination comprises detecting a first fluorescent dye specifically attached to said antibodies and a second fluorescent dye nonspecifically attached to said labeled antigens.

43. The method as provided in claim 1 wherein said providing step comprises providing a disk adapted for rotary motion.

44. The method as provided in claim 1 wherein said providing step comprises providing a photoslide adapted for substantially complete illumination.

45. The method as provided in claim 44 further comprising detecting the effect of illumination by sequentially detecting portions substantially smaller than the total area of said photoslide.

46. The method as provided in claim 26 further comprising the step of removing, prior to said illuminating step, substantially all unbound second labeled antibodies which have not reacted immunologically by spraying said surface means.

47. The method as provided in claim 26 further comprising the step of removing, prior to said illuminating step, substantially all unbound second labeled antibodies which have not reacted immunologically by washing and spraying said surface means.

48. The method as provided in claim 26 wherein the step of detecting the effect of said illumination comprises detecting light reflected from said surface means.

49. The method as provided in claim 26 wherein the step of detecting the effect of said illumination comprises detecting bulk fluorescence and intrinsic fluorescence of said surface means for use as a reference whereby the true level of bulk fluorescence may be assessed.

50. The method as provided in claim 26 wherein the step of detecting the effect of said illumination comprises a combination of detecting light scatter, bulk fluorescence, and intrinsic fluorescence of said surface means.

51. The method as provided in claim 23 wherein said providing step comprises providing surface means comprising a disk adapted for rotary motion.

52. The method as provided in claim 23 wherein said providing step comprises providing surface means comprising a photoslide, and said detecting the effect of illumination comprises sequentially detecting portions of said photoslide substantially smaller than the total area of said photoslide.

53. The method as provided in claim 33 further comprising the step of removing, prior to said illuminating steps, substantially all unbound second labeled antibodies which have not reacted immunologically by spraying said surface means.

54. The method as provided in claim 33 further comprising the step of removing, prior to said illuminating steps, substantially all unbound second labeled antibodies which have not reacted immunologically by washing and spraying said surface means.

55. The method as provided in claim 33 wherein the step of detecting the effect of said illumination comprises detecting light reflected from said surface means.

56. The method as provided in claim 33 wherein the step of detecting the effect of said illumination comprises detecting light transmitted through said surface means.

57. The method as provided in claim 33 wherein the step of detecting the effect of said illumination comprises detecting bulk fluorescence and intrinsic fluorescence of said surface means for use as a reference whereby the true level of bulk fluorescence may be assessed.

58. The method as provided in claim 33 wherein the step of detecting the effect of said illumination comprises detecting bulk fluorescence reflected from said surface means.

59. The method as provided in claim 30 wherein said providing step comprises providing surface means comprising a disk adapted for rotary motion.

60. The method as provided in claim 1 wherein the providing step comprises providing surface means having first antibodies specific for the antigen to be determined, said first antibodies attached to latex particles and said particles associated with said surface means in a specified pattern of areas, each area alternating with the presence and absence of said first antibodies.

61. The method as provided in claim 8 wherein the providing step comprises providing surface means having first antibodies specific for the antigens to be determined, said first antibodies attached to latex particles and said particles associated with said surface means in a specified pattern of areas, each area alternating with the presence and absence of said first antibodies.

62. The method as provided in claim 16 wherein the providing step comprises providing surface means having second antigens, said second antigens attached to latex particles and said particles associated with said surface means in a specified pattern of areas, each area alternating with the presence and absence of said second antigen.

63. The method as provided in claim 23 wherein the providing step comprises providing surface means having second antigens, said second antigens attached to latex particles and said particles associated with said surface means in a specified pattern of areas, each area alternating with the presence and absence of said second antigens.

64. The method as provided in claim 30 wherein the providing step comprises providing surface means having first antibodies, said first antibodies attached to latex particles and said particles associated with said surface means in a specified pattern of areas, each area alternating with the presence and absence of said first antibodies.

* * * * *